(12) United States Patent
Cheng et al.

(10) Patent No.: US 10,393,707 B2
(45) Date of Patent: Aug. 27, 2019

(54) METHOD FOR ESTIMATING A VARIATION IN PRELOAD APPLIED TO LINEAR GUIDEWAY

(71) Applicant: HIWIN TECHNOLOGIES CORP., Taichung (TW)

(72) Inventors: Chih-Chun Cheng, Taichung (TW); Ping-Chun Tsai, Taichung (TW); Wen-Nan Cheng, Taichung (TW); Yu-Hsin Kuo, Taichung (TW); Yin-Chun Cheng, Taichung (TW); Hsi-Hsun Cheng, Taichung (TW); Kuan-Te Yu, Taichung (TW)

(73) Assignee: Hiwin Technologies Corp., Taichung (TW)

( * ) Notice: Subject to any disclaimer, the term of this patent is extended or adjusted under 35 U.S.C. 154(b) by 132 days.

(21) Appl. No.: 15/585,583

(22) Filed: May 3, 2017

(65) Prior Publication Data
US 2018/0321194 A1 Nov. 8, 2018

(51) Int. Cl.
*G01N 29/14* (2006.01)
*G01N 29/44* (2006.01)

(52) U.S. Cl.
CPC ......... *G01N 29/4427* (2013.01); *G01N 29/14* (2013.01); *G01N 29/4472* (2013.01); *G01N 2291/2623* (2013.01)

(58) Field of Classification Search
CPC .... G01N 29/12; G01N 29/4427; G01N 29/14; G01N 29/46; G01M 13/02; G01M 13/028; G01M 13/045; F16H 25/22; G16H 25/2204
See application file for complete search history.

(56) References Cited

U.S. PATENT DOCUMENTS

| | | | | |
|---|---|---|---|---|
| 5,013,164 A * | 5/1991 | Tsukada | ................ | F16C 29/002 384/45 |
| 5,228,358 A * | 7/1993 | Sakino | ................ | B23Q 1/38 108/143 |
| 5,704,250 A * | 1/1998 | Black | ................ | B23Q 5/408 318/48 |
| 7,942,099 B2 * | 5/2011 | Ro | ................ | F16C 29/025 104/281 |
| 2003/0106375 A1 * | 6/2003 | Sabini | ................ | G01H 1/003 73/593 |
| 2005/0171736 A1 * | 8/2005 | Kang | ................ | G01H 1/006 702/185 |
| 2011/0081216 A1 * | 4/2011 | Ogura | ................ | B23Q 1/265 409/141 |

(Continued)

Primary Examiner — Helen C Kwok
(74) Attorney, Agent, or Firm — Michael Best & Friedrich LLP

(57) ABSTRACT

A method for estimating a variation in a preload applied to a linear guideway of a machine tool includes steps of: a) obtaining, via each of vibration sensors, first and second vibration signals that are generated according to detection of vibration of a table disposed on the linear guideway respectively at first and second time instants; b) determining, via the computation module, first and second natural frequencies based on a theoretical mode shape and respectively on the first and second vibration signals; and c) determining, via the computation module, the variation in the preload based on the first and second natural frequencies.

8 Claims, 3 Drawing Sheets

(56) References Cited

U.S. PATENT DOCUMENTS

| | | | | |
|---|---|---|---|---|
| 2013/0025896 A1* | 1/2013 | Pierse | ............... | B23Q 11/0025 173/152 |
| 2014/0076207 A1* | 3/2014 | Ro | ........................ | B23Q 1/58 108/20 |
| 2014/0229125 A1* | 8/2014 | Cheng | ............... | G01M 13/028 702/56 |
| 2015/0217379 A1* | 8/2015 | Kim | ................. | B23Q 11/0032 700/159 |
| 2015/0354690 A1* | 12/2015 | Cheng | .................. | G01N 29/14 73/587 |
| 2017/0292900 A1* | 10/2017 | Kuo | ...................... | G01M 7/08 |

* cited by examiner

METHOD FOR ESTIMATING A VARIATION IN PRELOAD APPLIED TO LINEAR GUIDEWAY

FIELD

The disclosure relates to a method for estimating a variation in a preload applied to a linear guideway, and more particularly to a method for estimating a variation in a preload applied to a linear guideway included in a machine tool.

BACKGROUND

A preload applied to a linear guideway included in a machine tool is gradually reduced due to wear and tear in use. When reduction of the preload reaches a certain amount, the linear guideway has to be replaced by a new one.

A conventional method for estimating a variation in the preload requires the linear guideway to be removed from the machine tool before the preload can be measured by a measuring tool. To monitor the variation in the preload, the preload has to be measured repeatedly, and hence the linear guideway has to be removed from the machine tool regularly. The conventional method is consequently time-consuming and inconvenient.

SUMMARY

Therefore, an object of the disclosure is to provide a method for estimating a variation in a preload applied to at least one linear guideway included in a machine tool that can alleviate at least one drawback of the prior art.

According to the disclosure, the method is to be implemented by a plurality of vibration sensors and a computation module. The machine tool further includes a table disposed on the at least one linear guideway. The vibration sensors are disposed on the table. The method includes steps of:

a) obtaining, via each of the plurality of vibration sensors, a first vibration signal that is generated according to detection of vibration of the table by the vibration sensor at a first time instant;

b) determining, via the computation module, at least one first natural frequency that is associated with the table based on the first vibration signals and at least one theoretical mode shape that is associated with the table;

c) obtaining, via each of the plurality of vibration sensors, a second vibration signal that is generated according to detection of vibration of the table by the vibration sensor at a second time instant;

d) determining, via the computation module, at least one second natural frequency that is associated with the table based on the second vibration signals and the at least one theoretical mode shape; and e) determining, via the computation module, the variation in the preload applied to the at least one linear guideway based on the at least one first natural frequency and the at least one second natural frequency.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
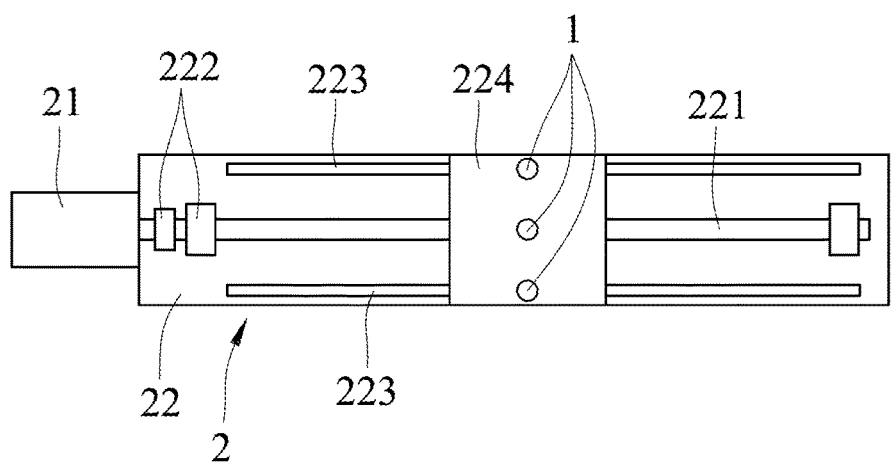
FIG. 1 is a schematic diagram illustrating a top view of a machine tool and a plurality of vibration sensors disposed on a table of the machine tool.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, an embodiment of a plurality of vibration sensors 1 and a computation module (not shown) that are used to implement a method for estimating a variation in a preload applied to at least one linear guideway included in a machine tool 2 is illustrated. The vibration sensors 1 are connected to the computation module. The computation module may be implemented by a microcontroller of a mobile device, a central processing unit (CPU) of a personal computer (PC), or a System on Chip (SoC), but is not limited thereto. In this embodiment, the computation module includes a general purpose computer.

The machine tool 2 is a conventional machine tool, and includes a motor 21 and a feeding unit 22. The feeding unit 22 includes a screw 221 connected to the motor 21, a plurality of bearings 222 pivotally connected to the screw 221, two linear guideways 223, and a table 224 disposed on the linear guideways 223. The table 224 is actuable by the screw 221 to slidably move along the linear guideways 223. Each of the linear guideways 223 is initially applied with a preload in equal amount.

The vibration sensors 1 are disposed on the table 224 so as to detect vibration of the table 224. In this embodiment, the vibration sensors 1 are exemplified by three in number, but are not limited thereto as long as the vibration sensors 1 are plural in number.

Figure 2:
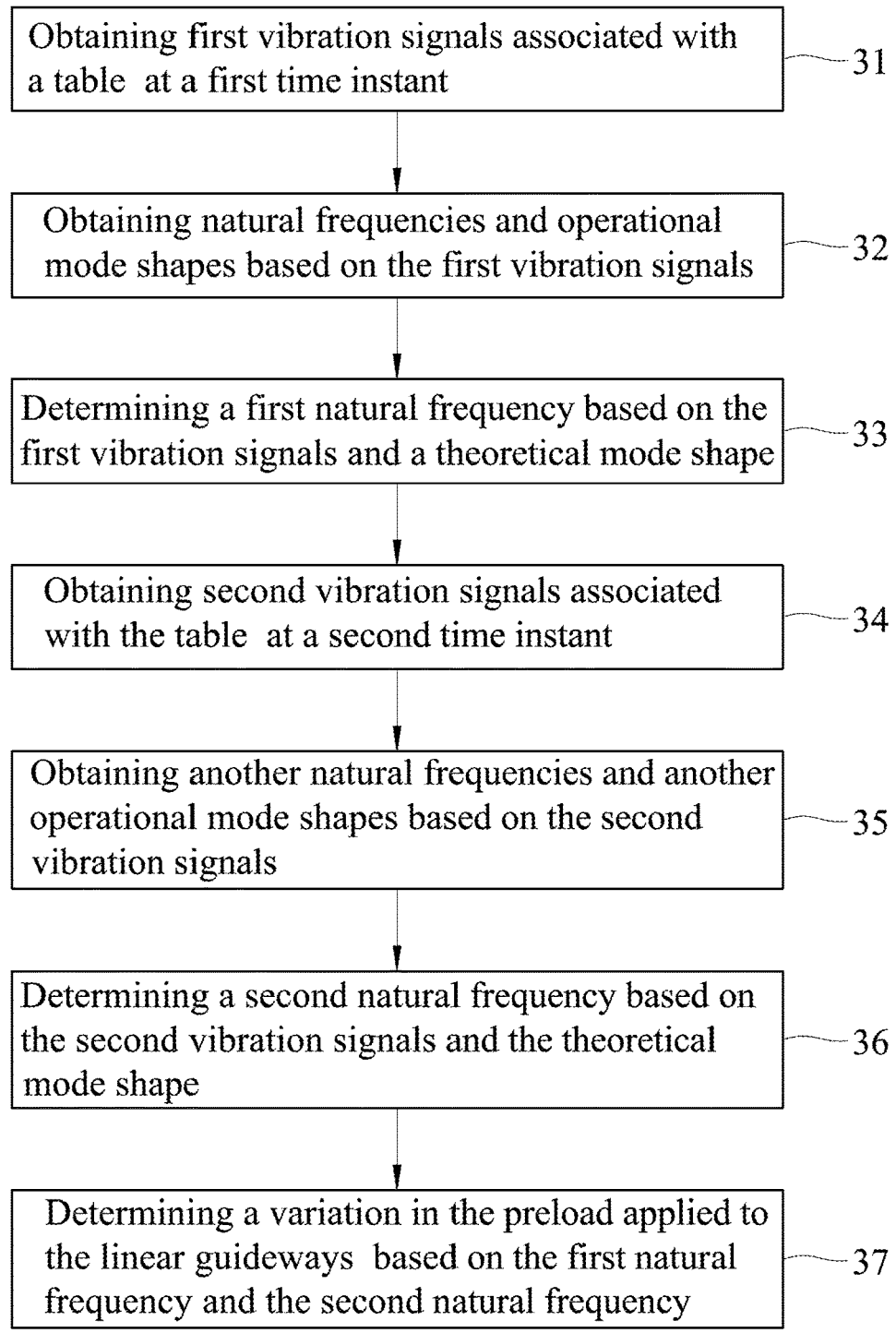
FIG. 2 is a flow chart illustrating an embodiment of a method for estimating a variation in a preload applied to at least one linear guideway included in the machine tool according to the disclosure.

Referring to FIG. 2, an embodiment of the method according to the disclosure is illustrated. The method includes the following steps 31-37.

In step 31, the motor 21 excites the feeding unit 22 at a first time instant so that the table 224 vibrates. The computation module obtains, via each of the vibration sensors 1, a first vibration signal that is generated according to detection of vibration of the table 224 by the vibration sensor 1 at the first time instant. It is noted that implementation of exciting the feeding unit 22 may vary in other embodiments. For example, an external vibration exciter that does not belong to the machine tool 2 may be utilized to excite the feeding unit 22 so as to make the table 224 vibrate.

In step 32, the computation module performs an operational modal analysis (OMA) on the first vibration signals obtained in step 31 to obtain a plurality of natural frequencies that are associated with the table 224 and to obtain a plurality of operational mode shapes that correspond respectively to the plurality of natural frequencies. The OMA is well known for people who are skilled in the art, but a brief introduction thereof will be provided herein for clarifying details of this disclosure.

Figure 3:
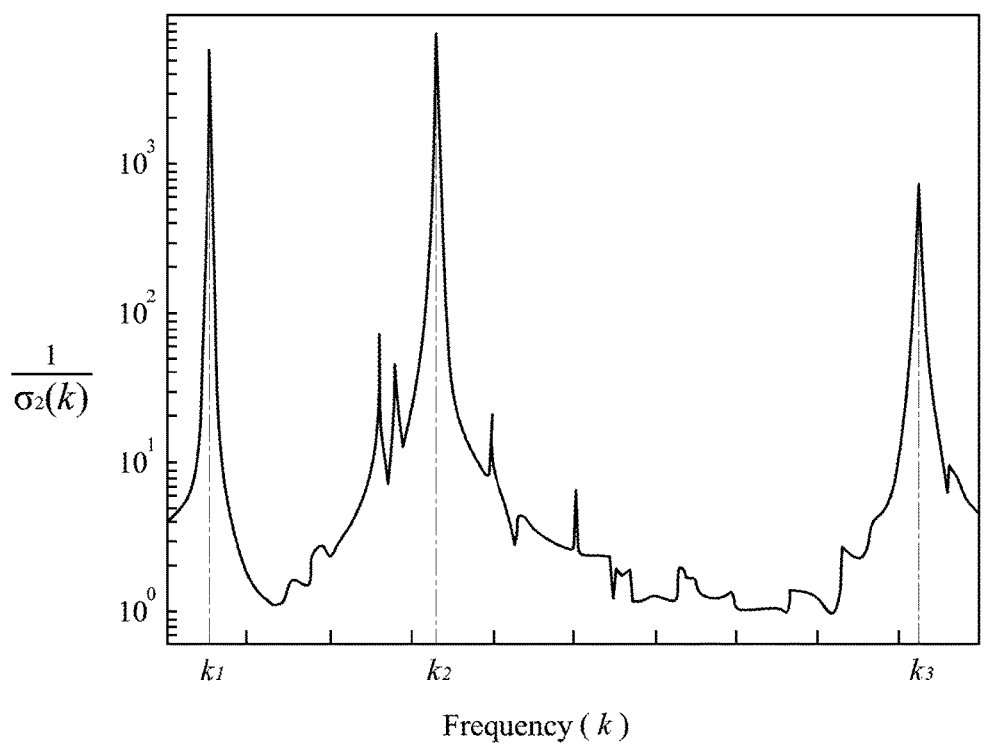
FIG. 3 is a schematic diagram illustrating a relationship between natural frequencies associated with the table and the reciprocal of a singular value $\sigma_2(k)$.

Assuming that the first vibration signals are respectively denoted as $X_1(k)$, $X_2(k)$ and $X_3(k)$ in frequency domain, where k represents frequency. Based on the first vibration signals $X_1(k)$, $X_2(k)$ and $X_3(k)$, quantities of displacement transmissibility $$T_{12}(k) = \frac{G(X_1(k), X_2(k))}{G(X_1(k), X_1(k))}, \ T_{13}(k) = \frac{G(X_1(k), X_3(k))}{G(X_1(k), X_1(k))} \text{ and}$$

$$T_{23}(k) = \frac{G(X_2(k), X_3(k))}{G(X_2(k), X_2(k))}$$

that are associated with the table 224 are correspondingly computed, where G represents a power spectrum density function. For each value of the frequency k, a matrix $[T(k)]=[T_{12}(k), T_{13}(k), T_{23}(k), 1]^T$ is performed with singular value decomposition (SVD) so that a result of decomposition $[T(k)]=[U(k)][\Sigma(k)][V(k)]^T$ is obtained, where $U(k)$ and $V(k)$ are unitary matrices, $$[\Sigma(k)] = \begin{bmatrix} \sigma_1(k) & 0 & \cdots & 0 \\ 0 & \sigma_2(k) & \cdots & 0 \\ \vdots & \vdots & \ddots & \vdots \\ 0 & 0 & \cdots & \sigma_n(k) \end{bmatrix}$$

represents a singular value matrix, and $\sigma_1(k) \geq \sigma_2(k) \geq \cdots \sigma_n(k)$ represent singular values. Therefore, a curve of the reciprocal of the singular value $\sigma_2(k)$, i.e., $$\frac{1}{\sigma_2(k)},$$

for different values of the frequency k can be obtained as what is shown in FIG. 3. Each value of the frequency k corresponding to a peak of the curve is a natural frequency, e.g., $k_1$, $k_2$ and $k_3$ shown in FIG. 3. The operational mode shape corresponding to one natural frequency is an eigenvector corresponding to the singular value calculated in SVD for that natural frequency. For example, each of the operational mode shapes corresponding to a respective one of the natural frequencies $k_1$, $k_2$ and $k_3$ is the eigenvector corresponding to a respective one of the singular values $\sigma_2(k_1)$, $\sigma_2(k_2)$ and $\sigma_2(k_3)$.

In step 33, the computation module determines at least one first natural frequency that is associated with the table 224 based on the first vibration signals and at least one theoretical mode shape that is associated with the table 224. The at least one theoretical mode shape, which approximates a most reasonable way of the vibration of the table 224, is determined in advance by a finite element method (FEM). Since FEM is well known for people who are skilled in the art, details thereof will be omitted herein. In this embodiment, the at least one theoretical mode shape is singular in number, but is not limited thereto.

Specifically speaking, the computation module selects the at least one first natural frequency among the plurality of natural frequencies based on similarity between each of the operational mode shapes and the theoretical mode shape. In this embodiment, the at least one first natural frequency is singular in number, but is not limited thereto. In other words, the computation module selects the first natural frequency from among the plurality of natural frequencies by locating one of the natural frequencies which corresponds to one of the plurality of operational mode shapes between which and the theoretical mode shape the similarity is the greatest among the plurality of operation mode shapes, and making said one of the natural frequencies serve as the first natural frequency.

In this embodiment, the similarity is associated with a modal assurance criterion (MAC) between the theoretical mode shape and each the plurality of operational mode shapes. A MAC between a modal vector $\vec{u}$ and another modal vector $\vec{v}$ is calculated by $$MAC(\vec{u}, \vec{v}) = \frac{|\vec{u}^T \vec{v}^*|^2}{(\vec{u}^T \vec{v}^*)(\vec{u}^T \vec{v}^*)}.$$

A greater MAC in value means a lower degree of orthogonality and a higher degree of similarity. Therefore, in one embodiment, given that a vector a represents the theoretical mode shape, and that a plurality of vectors $\vec{b}_1, \vec{b}_2, \ldots, \vec{b}_m$ represent the operational mode shapes determined in step 32, the first natural frequency can be determined by calculating $\{MAC(\vec{a}, \vec{b}_i) | i=1, 2, \ldots, m\}$ and selecting one of the natural frequencies which corresponds to one of the plurality of vectors $\vec{b}_1, \vec{b}_2, \ldots, \vec{b}_m$ that results in the greatest value of the MAC to serve as the first natural frequency.

In step 34, the motor 21 excites the feeding unit 22 at a second time instant which is subsequent to the first time instant so that the table 224 vibrates. The computation module obtains, via each of the vibration sensors 1, a second vibration signal that is generated according to detection of vibration of the table 224 by the vibration sensor 1 at the second time instant.

In step 35, in a way similar to processing the first vibration signals, the computation module performs the OMA on the second vibration signals to obtain another plurality of natural frequencies that are associated with the table 224 and to obtain another plurality of operational mode shapes that correspond respectively to the another plurality of natural frequencies.

In step 36, the computation module determines at least one second natural frequency that is associated with the table 224 based on the second vibration signals and the theoretical mode shape discussed in step 33. The computation module selects the at least one second natural frequency from among the another plurality of natural frequencies based on the similarity between each of the another plurality of operational mode shapes and the theoretical mode shape. In this embodiment, the at least one second natural frequency is singular in number, but is not limited thereto.

As what has been mentioned previously, the computation module selects the second natural frequency from among the another plurality of natural frequencies by locating one of the another plurality of natural frequencies that corresponds to one of the another plurality of operational mode shapes between which and the theoretical mode shape the similarity is the greatest among the another plurality of operational mode shapes, and making said one of the another natural frequencies serve as the second natural frequency. The similarity is associated with the MAC between each of the another plurality of operational mode shapes and the theoretical mode shape. Since the way of determining the similarity based on the MAC has been addressed, details thereof will be omitted herein.

In step 37, the computation module determines the variation in the preload applied to the linear guideways 223 of the machine tool 2 based on the first natural frequency and the second natural frequency.

Specifically speaking, the computation module determines, when it is determined that the second natural frequency is smaller than the first natural frequency, that there is a reduction in the preload applied to the linear guideways 223. The reduction is associated with a ratio of a difference between the first and second natural frequencies to the first natural frequency.

In other words, assuming that at the first time instant when the linear guideways 223 have just been installed to the machine tool 2, the preload applied to the linear guideways 223 has an initial value in magnitude, the computation module is capable of estimating, based on the initial value of the preload and the ratio of the difference between the first and second natural frequencies to the first natural frequency, the magnitude of the preload applied to the linear guideways 223 at the second time instant when the machine tool 2 has operated for a while without requiring the linear guideways 223 to be removed from the machine tool 2.

In some embodiments, a plurality of theoretical mode shapes associated with the table 224 are determined in advance by FEM. The computation module computes a value of the MAC between each of the theoretical mode shapes and each of operational mode shapes determined based on first vibration signals. Next, the computation module selects a first natural frequency from among a plurality of natural frequencies with the first natural frequency corresponding to the operational mode shape which results in the greatest value of MAC. Likewise, the computation module computes a value of the MAC between each of the theoretical mode shapes and each of operational mode shapes determined based on second vibration signals, and then selects a second natural frequency from among another plurality of natural frequencies with the second natural frequency corresponding to the operational mode shape which results in the greatest value of MAC.

In other words, given that a plurality of vectors $\vec{a}_1$, $\vec{a}_2, \ldots, \vec{a}_p$ represent the theoretical mode shapes, and that a plurality of vectors $\vec{b}_1, \vec{b}_2, \ldots, \vec{b}_m$ represent the operational mode shapes determined based on the first vibration signals, the first natural frequency can be determined by calculating $\{MAC(\vec{a}_j, \vec{b}_i) | i=1, 2, \ldots, m; j=1, 2, \ldots, p\}$ and selecting one of the natural frequencies which corresponds to one of the plurality of vectors $\vec{b}_1, \vec{b}_2, \ldots, \vec{b}_m$ that results in the greatest value of MAC to serve as the first natural frequency. The second natural frequency is determined in a similar way and details thereof will be omitted herein.

In some embodiments, a plurality of first natural frequencies at the first time instant are determined based on a plurality of theoretical mode shapes that are associated with the table 224 and that are determined in advance by FEM, and based on a plurality of operational mode shapes that are determined according to first vibration signals; a plurality of second natural frequencies at the second time instant are determined based on the plurality of the theoretical mode shapes, and based on another plurality of the operational mode shapes that are determined according to second vibration signals. After that, the ratio of reduction from the magnitude of the preload applied to the linear guideways 223 at the first time instant to that at the second time instant can be determined based on the first natural frequencies and the second natural frequencies.

For example, two operational mode shapes, which result respectively in the first and second greatest values of MAC and which are respectively represented by two vectors $\vec{c}_1$ and $\vec{c}_2$, are selected from among the plurality of the operational mode shapes determined based on the first vibration signals. Next, two natural frequencies which correspond to the two operational mode shapes are designated to serve as two first natural frequencies, wherein the natural frequency corresponding to the vector $\vec{c}_1$ is smaller than the natural frequency corresponding to the vector $\vec{c}_2$.

Similarly, another two operational mode shapes, which result respectively in the first and second greatest values of MAC and which are respectively represented by two vectors $\vec{d}_1$ and $\vec{d}_2$, are selected from among the plurality of the operational mode shapes determined based on the second vibration signals. Next, another two natural frequencies corresponding to the another two operational mode shapes are designated to serve as two second natural frequencies, wherein the natural frequency corresponding to the vector $\vec{d}_1$ is smaller than the natural frequency corresponding to the vector $\vec{d}_2$.

Thereafter, a matrix $[\vec{c}_1, \vec{c}_2, \vec{d}_1, \vec{d}_2]^T$ is used as an input of a pre-trained classifier of predictive modeling, such as an artificial neural network technique or a linear regression technique, to predict the variation in the preload applied to the linear guideways 223 of the machine tool 2 between the first and second time instants.

In summary, the method for estimating a variation in a preload applied to at least one linear guideway of a machine tool according to the disclosure includes the following steps. The computation module determines at least one first natural frequency associated with the table at a first time instant based on at least one theoretical mode shape and first vibration signals. The computation module determines at least one second natural frequency associated with the table at a second time instant based on the at least one theoretical mode shape and second vibration signals. The computation module determines the variation in the preload based on the at least one first natural frequency and the at least one second natural frequency, without requiring the at least one linear guideway to be removed from the machine tool.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A method for estimating a variation in a preload applied to at least one linear guideway included in a machine tool, the method to be implemented by a plurality of vibration sensors and a computation module, the machine tool further including a table disposed on the at least one linear guideway, the plurality of vibration sensors being disposed on the table, the method comprising steps of:
   a) obtaining, via each of the plurality of vibration sensors, a first vibration signal that is generated according to detection of vibration of the table by the vibration sensor at a first time instant;
   b) determining, via the computation module, at least one first natural frequency that is associated with the table based on the first vibration signals obtained in step a) and at least one theoretical mode shape that is associated with vibration of the table;
   c) obtaining, via each of the plurality of vibration sensors, a second vibration signal that is generated according to detection of vibration of the table by the vibration sensor at a second time instant;
   d) determining, via the computation module, at least one second natural frequency that is associated with the table based on the second vibration signals obtained in step c) and the at least one theoretical mode shape; and
   e) determining, via the computation module, the variation in the preload applied to the at least one linear guideway based on the at least one first natural frequency and the at least one second natural frequency.

2. The method as claimed in claim 1, wherein:
step b) includes
   performing an operational modal analysis (OMA) on the first vibration signals to obtain a plurality of natural frequencies that are associated with the table and to obtain a plurality of operational mode shapes that correspond respectively to the plurality of natural frequencies, and
   selecting the at least one first natural frequency from among the plurality of natural frequencies based on similarity between each of the operational mode shapes and the at least one theoretical mode shape; and
step d) includes
   performing the OMA on the second vibration signals to obtain another plurality of natural frequencies that are associated with the table and to obtain another plurality of operational mode shapes that correspond respectively to the another plurality of natural frequencies, and
   selecting the at least one second natural frequency from among the another plurality of natural frequencies based on similarity between each of the another plurality of operational mode shapes and the at least one theoretical mode shape.

3. The method as claimed in claim 2, wherein:
   the at least one first natural frequency and the at least one second natural frequency are both singular in number;
   the step of selecting the at least one first natural frequency includes selecting one of the plurality of natural frequencies that corresponds to one of the plurality of operational mode shapes, where the similarity between the at least one theoretical mode shape and the one of the plurality of operational mode shapes is greater than similarity between the at least one theoretical mode shape and any of the rest of the plurality of operational mode shapes, to serve as the first natural frequency; and
   the step of selecting the at least one second natural frequency includes selecting one of the another plurality of natural frequencies that corresponds to one of the another plurality of operational mode shapes, where the similarity between the at least one theoretical mode shape and the one of the another plurality of operational mode shapes is greater than similarity between the at least one theoretical mode shape and any of the rest of the another plurality of operational mode shapes, to serve as the second natural frequency.

4. The method as claimed in claim 3, wherein step e) includes determining, when the computation module determines that the second natural frequency is smaller than the first natural frequency, that there is a reduction in the preload applied to the at least one linear guideway of the machine tool.

5. The method as claimed in claim 4, wherein in step e), the reduction is associated with a ratio of a difference between the first and second natural frequencies to the first natural frequency.

6. The method as claimed in claim 2, wherein:
   in step b), the similarity is associated with a modal assurance criterion (MAC) between each the plurality of operational mode shapes and the at least one theoretical mode shape; and
   in step d), the similarity is associated with an MAC between each of the another plurality of operational mode shapes and the at least one theoretical mode shape.

7. The method as claimed in claim 1, wherein:
   the at least one first natural frequency determined in step b) and the at least one second natural frequency determined in step d) are both singular in number; and
   step e) includes determining, when the computation module determines that the second natural frequency is smaller than the first natural frequency, that there is a reduction in the preload applied to the at least one linear guideway of the machine tool.

8. The method as claimed in claim 7, wherein in step e), the reduction is associated with a ratio of a difference between the first and second natural frequencies to the first natural frequency.

* * * * *